(12) United States Patent
Elaissari et al.

(10) Patent No.: US 7,217,457 B2
(45) Date of Patent: May 15, 2007

(54) COMPOSITE PARTICLES, DERIVED CONJUGATES, PREPARATION METHOD AND APPLICATIONS

(75) Inventors: Abdelhamid Elaissari, Saint Genis Laval (FR); Franck Montagne, Charly (FR); Eric Bosc, Salles (FR); Christian Pichot, Corbas (FR); Bernard Mandrand, Villeurbanne (FR); Jérôme Bibette, Bordeaux (FR); Olivier Mondain-Monval, Bordeaux (FR)

(73) Assignees: Bio Merieux, Marcy l'Etoile (FR); Centre National de la Recherche Scientifique, Paris (FR)

( * ) Notice: Subject to any disclaimer, the term of this patent is extended or adjusted under 35 U.S.C. 154(b) by 200 days.

(21) Appl. No.: 10/475,709

(22) PCT Filed: May 6, 2002

(86) PCT No.: PCT/FR02/01552

§ 371 (c)(1),
(2), (4) Date: Feb. 4, 2004

(87) PCT Pub. No.: WO03/004559

PCT Pub. Date: Jan. 16, 2003

(65) Prior Publication Data

US 2004/0115433 A1 Jun. 17, 2004

(30) Foreign Application Priority Data

May 10, 2001 (FR) .................................. 01 06203

(51) Int. Cl.
*B32B 5/16* (2006.01)
*C08K 3/00* (2006.01)

(52) U.S. Cl. ..................... 428/407; 524/401; 524/457; 524/481

(58) Field of Classification Search ................ 428/402, 428/403, 407; 427/212, 221; 524/401, 457, 524/481
See application file for complete search history.

(56) References Cited

U.S. PATENT DOCUMENTS

| | | | | |
|---|---|---|---|---|
| 4,358,388 A * | 11/1982 | Daniel et al. | ............ | 252/62.54 |
| 4,952,622 A * | 8/1990 | Chauvel et al. | ............. | 524/376 |
| 5,356,713 A * | 10/1994 | Charmot et al. | ............ | 428/407 |
| 5,834,121 A * | 11/1998 | Sucholeiki et al. | ......... | 428/407 |
| 6,133,047 A * | 10/2000 | Elaissari et al. | ............ | 436/526 |
| 6,383,500 B1 * | 5/2002 | Wooley et al. | .............. | 428/407 |
| 6,491,903 B1 * | 12/2002 | Forster et al. | ........... | 424/78.01 |
| 6,521,341 B1 * | 2/2003 | Elaissari et al. | ............ | 428/403 |
| 6,627,314 B2 * | 9/2003 | Matyjaszewski et al. | ... | 428/403 |
| 6,649,138 B2 * | 11/2003 | Adams et al. | .............. | 423/403 |
| 6,866,838 B1 * | 3/2005 | Mondain-Monval et al. | ............ | 424/9.52 |
| 7,001,589 B2 * | 2/2006 | Mondain-Monval et al. | ............ | 424/9.52 |
| 2004/0191518 A1 * | 9/2004 | Naito et al. | ................. | 428/407 |

FOREIGN PATENT DOCUMENTS

EP 0390634 A * 3/1990

* cited by examiner

Primary Examiner—H. Thi Le
(74) Attorney, Agent, or Firm—Oliff & Berridge PLC

(57) ABSTRACT

The invention relates to composite particles comprising a hydrophobic polymer core and inorganic nanoparticles. Said hydrophobic polymer forms a polymer matrix inside which the inorganic nanoparticles are stabilized and distributed in a relatively homogenous manner. Said particles are at least partially surrounded by an amphophilic copolymer comprising a hydrophobic part and a hydrophilic part, said hydrophobic part being at least partially immobilized in the polymer matrix. The inventor also relates to the preparation method thereof, the conjugates comprising such particles and a ligand and the use of same in reactants and therapeutic compositions.

50 Claims, No Drawings

COMPOSITE PARTICLES, DERIVED CONJUGATES, PREPARATION METHOD AND APPLICATIONS

A subject matter of the present invention is composite particles, their process of preparation and their uses.

Microspheres of polymer type are of advantage as support, carrier or vehicle in the fields of biological engineering, diagnosis and pharmaceuticals. To this end, they have been used in medical diagnostics as solid support for biological molecules.

Colloidal particles have a number of advantages in comparison with conventional solid supports, such as tubes, sheets or beads, in particular because they make it possible to have available a large surface area for specific interactions and because they can be easily modified chemically in order to introduce, at their surface, functional groups capable of reacting with other molecules, for example biological molecules, such as antibodies or fragments of antibodies, proteins, polypeptides, polynucleotides, nucleic acids, fragments of nucleic acids, enzymes or chemical molecules, such as catalysts, medicaments, cage molecules or chelating agents.

Among colloidal particles, magnetic latices have aroused great interest in the analytical field and are used, for example, as means for separating and/or detecting analytes, such as antigens, antibodies, biochemical molecules, nucleic acids and others.

Composite particles of polymer/magnetic type are usually classified into three categories on the criterion of size: small particles having a diameter of less than 50 nm, large particles having a diameter of greater than 2 µm and intermediate particles with a diameter of between 50 and 1000 nm.

However, in order for them to be able to be regarded as good candidates, in particular for a diagnostic application, they have to meet certain criteria. From a morphological viewpoint, it is preferable for them to be relatively spherical and for the magnetic filler to be distributed relatively homogeneously in the polymer matrix. They must not aggregate irreversibly under the action of a magnetic field, which means that they can be easily, rapidly and reversibly redispersed. Likewise, they must exhibit a relatively low density in order to reduce the phenomenon of sedimentation. Advantageously, they should exhibit a narrow particle size distribution. Monodisperse or isodisperse particles are terms also used.

Thus, because of their size and their density, large magnetic particles in suspension in a liquid phase have a tendency to rapidly sediment. Furthermore, they tend to aggregate after having been subjected to a magnetic field because they are liable to have been, for this reason, magnetized permanently (residual magnetism). They therefore do not constitute a good candidate.

On the other hand, small magnetic particles have a tendency to remain in suspension because of their Brownian motion and are difficult to attract, indeed even are not attracted at all, by a magnet, in particular if the magnetic field applied is relatively weak. They are therefore not very appropriate for the uses enlarged upon above.

There is therefore an obvious advantage in producing composite particles of polymer/magnetic type, exhibiting a size intermediate between 50 and 1000 nm, which simultaneously overcome the above-mentioned disadvantages and meet the criteria established above. However, the invention is not limited to magnetizable composite particles, as described below.

Patent application EP-A-0 390 634 discloses magnetizable composite microspheres of hydrophobic crosslinked vinylaromatic polymer with a diameter of the order of 50 to 10000 nm and comprising a solid core composed of magnetizable particles and of a shell composed of a hydrophobic polymer derived from at least one hydrophobic vinylaromatic monomer and from at least one polyethylenically unsaturated emulsifying polymer which is soluble in the vinylaromatic monomer(s) and which is capable of crosslinking with said monomer(s). However, although they may meet the requirements of size, they exhibit the disadvantage of not having a homogeneous distribution of the magnetic filler which is located inside the core. Furthermore, and as clearly emerges from the appended figures, the particles are not homogeneous in size. They are thus a collection of polydisperse particles which will have to be sorted by application of a magnetic field in order to retain only the particles with the required size.

Mention may also be made of Dynal (trade name) particles. These particles are microspheres composed of a porous core of polystyrene and of iron oxides, the iron oxides having been deposited by impregnation in the pores available at the surface of the polystyrene, and of a covering made of another polymer which encapsulates the iron oxides of the porous microspheres. They exhibit a diameter of 2.8 µm (M280 particles) and of 4.5 µm (M450 particles) respectively and are relatively uniform in size. They are therefore regarded as isodisperse particles but, because of their large size, exhibit the abovementioned disadvantages, mainly the phenomenon of sedimentation. Furthermore, their specific surface is low.

The document U.S. Pat. No. 4,358,388 discloses composite particles composed of a polymer matrix in which a magnetic filler is homogeneously distributed. They are obtained by polymerization of a water-insoluble organic monomer in an organic phase comprising the magnetic filler, said organic phase being in emulsion in an aqueous phase in the presence of a surface-active agent.

Such particles constitute, in biology, supports similar to those mentioned above of the tube, sheet or bead type, with an additional asset residing in their ability to be easily isolated by the application of a magnetic field.

Nevertheless, their use in this field of application remains fairly limited as these particles exhibit no functionalization.

According to the invention, novel composite particles are now available which introduce a solution to the problems posed by the known particles described above and which meet the following criteria:

- isodisperse spherical particles,
- particles having an inorganic filler homogeneously distributed in the core,
- particles of intermediate size, namely having a diameter of between 50 and 1000 nm,
- functionalized or functionalizable particles,
- the inorganic filler can be magnetic or magnetizable,
- particles obtained by a simple and controllable synthetic process.

The composite particles of the invention comprise a core made of a hydrophobic polymer and inorganic nanoparticles, said hydrophobic polymer constituting a polymer matrix within which the inorganic nanoparticles are stabilized and distributed homogeneously, said particles being at least partially surrounded by an amphiphilic copolymer comprising a hydrophobic part and a hydrophilic part, the hydrophobic part of which is at least partially immobilized on or in said polymer matrix.

According to an alternative form of the invention, the particles are completely surrounded by the amphiphilic copolymer and/or all the hydrophobic part of the amphiphilic copolymer is immobilized on or in the polymer matrix.

An amphiphilic copolymer is understood, according to the invention, as a copolymer having a hydrophobic part and a hydrophilic part, it being understood that the hydrophobic part and/or the hydrophilic part can be a combination of constituent subparts of the amphiphilic copolymer which are respectively hydrophobic and/or hydrophilic. Thus, an amphiphilic copolymer of the invention is chosen in particular from block copolymers, sequential copolymers, branched polymers, the backbone of which is hydrophobic or hydrophilic and the branches of which are respectively hydrophilic or hydrophobic, or comb polymers, the backbone of which is hydrophobic or hydrophilic and the comb branches of which are respectively hydrophilic or hydrophobic.

The hydrophilic part of the amphiphilic copolymer can be ionic, anionic or cationic, or nonionic; it comprises functional groups which are reactive, directly or indirectly.

According to the invention, the hydrophobic part is at least partially immobilized on or in the polymer matrix. The immobilization of this hydrophobic part is always at least physical in nature and more specifically mechanical in nature, of the confinement type, and can complement a preliminary attachment of the hydrophobic part which is chemical or physical in nature, such as attachment by adsorption, for example. Thus, an immobilization can result from the following events:
- the hydrophobic part of the amphiphilic copolymer is adsorbed at the surface of the matrix and then permanently immobilized in the matrix by the hydrophobic polymer;
- said hydrophobic part is dissolved in the organic phase and then confined in the hydrophobic polymer during the formation of the matrix;
- said hydrophobic part is exclusively confined mechanically during the formation of the polymer matrix.

This immobilization results in particles having a high stability and in particular a stability much better than that of the known particles described above.

An appropriate amphiphilic copolymer advantageously comprises:
- a hydrophobic part chosen from polystyrenes, polyalkyls, such as polyethylene, or fatty acid chains, and/or
- a hydrophilic part chosen from poly(acrylic acid)s, polysulfates, polyamines, polyamides or polysaccharides.

The inorganic materials constituting the nanoparticles are chosen from metal oxides, such as iron, titanium, chromium, cobalt, zinc, copper, manganese or nickel oxides, and in particular from magnetizable metal oxides, such as iron oxides, magnetite or hematite; ferrites, such as manganese, nickel or manganese-zinc ferrites; or alloys of cobalt, of nickel.

The inorganic materials are advantageously chosen from magnetizable metal oxides, preferably from iron oxides.

The inorganic nanoparticles represent 5 to 95%, preferably 10 to 90% and advantageously 20 to 90% by mass, with respect to the total mass of the composite particle, preferably 25 to 85%.

Inside the particles of the invention, the nanoparticles are stabilized by stabilizing agents chosen from amphiphilic polymer chains or surface-active agents which are ionic or nonionic, functional or nonfunctional and polymerizable or nonpolymerizable. The functional surface-active agents are chosen in particular from fatty acids or fatty acid derivatives, in particular oleic acid or its derivatives, and the mixtures of surface-active agents as defined above.

The appropriate hydrophobic polymers of the matrix are polymers of hydrophobic vinylaromatic type, that is to say homopolymers of water-insoluble vinylaromatic monomers, such as styrene, methylstyrene, ethylstyrene, tert-butylstyrene or vinyltoluene, and the copolymers of these monomers with one another and/or with other comonomers, such as alkyl acrylates and methacrylates in which the alkyl group comprises from 3 to 10 carbon atoms, alkyl esters of ethylenic acids, the ethylenic acid possessing 4 or 5 carbon atoms and the alkyl group possessing 1 to 8 carbon atoms, methacrylic acids, styrene derivatives or diene compounds. Preferably, the polymer is a crosslinked polymer. This is obtained by adding, to the monomer(s), a small amount (less than 10% by weight) of molecules having at least two reactive double bonds, such as divinylbenzene, vinyl methacrylate, triallyl cyanurate, monoethylene glycol diacrylate or polyethylene glycol diacrylate.

The composite particles of the invention can also include a tracer, such as a radioactive tracer, it being understood that the tracer is introduced during the preparation of the emulsion as described in the following example 1.

The particles of the invention exhibit a diameter of the order of approximately 50 to 1000 nm, preferably of approximately 100 to 500 nm and advantageously of approximately 100 to 250 nm. This diameter is defined to plus or minus approximately 5%, which means that their volume-average diameter is defined to within plus or minus approximately 5%.

Another subject matter of the present invention is a process of the preparation of the above-mentioned composite particles which makes it possible to directly obtain isodisperse particles with a desired diameter without requiring a stage of sorting according to the diameter.

According to a first process of the invention, composite particles for which the hydrophobic part of the amphiphilic copolymer is at least partially immobilized in the polymer matrix are obtained as follows:
(i) a stable and isodisperse starting emulsion composed of two immiscible phases, a hydrophobic phase A composed of droplets comprising inorganic nanoparticles dispersed in an organic phase comprising a surface-active agent and a hydrophilic phase B in which the phase A is dispersed, is present;
(ii) hydrophobic monomers and at least one initiator are introduced into the phase B; and
(iii) said hydrophobic monomers are polymerized inside the phase A, and, according to this process, at least one amphiphilic copolymer is additionally introduced into the phase B before stage (iii), that is to say before or after stage (ii).

According to a second process of the invention, composite particles for which the hydrophobic part of the amphiphilic copolymer is at least partially immobilized on the polymer matrix are obtained as follows:
(i) a stable and isodisperse starting emulsion composed of two immiscible phases, a hydrophobic phase A composed of droplets comprising inorganic nanoparticles dispersed in an organic phase comprising a surface-active agent and a hydrophilic phase B in which the phase A is dispersed, is present;
(ii) hydrophobic monomers and at least one initiator are introduced into the phase B;

(iii) a fraction of said hydrophobic monomers is polymerized inside the phase A, and, according to this process, at least one amphiphilic copolymer is additionally introduced into the phase B before stage (iii) or after stage (iii) and then, during a stage (iv), the remaining fraction of the hydrophobic monomers is polymerized at the surface of the polymer matrix. When the amphiphilic copolymer is introduced before stage (iii), it can be introduced before or after stage (ii).

In order to obtain the composite particles according to the processes of the invention, the amphiphilic polymer is advantageously chosen from those set out above in the description of the composite particles.

The monomers employed must form hydrophobic polymers. They are insoluble in the hydrophilic phase and are chosen from vinylaromatic monomers, such as styrene, methylstyrene, ethylstyrene, tert-butylstyrene, aminomethylstyrene or vinyltoluene. They are used alone or as a mixture or alternatively as a mixture with other water-insoluble polymerizable monomers, such as alkyl acrylates, alkyl methacrylates, alkyl esters of ethylenic acids, methacrylic acids, styrene derivatives, ethylenic acids or diene compounds.

It is possible to add a hydrophobic crosslinking agent, for example a crosslinking monomer of divinylbenzene or dimethacrylate type, in particular vinyl dimethacrylate, to the monomer or to the mixture of monomers.

The organosoluble initiator is chosen from initiators of azobis type, such as 2,2'-azobis(2,4-dimethylvaleronitrile), 2,2'-azobis(4-methoxy-2,4-dimethylvaleronitrile), 2,2'-azobis(2-cyclopropylpropionitrile), 2,2'-azobis(2-methylpropionitrile), 2,2'-azobis(2-methylbutyronitrile), 1,1'-azobis(cyclohexane-1-carbonitrile), 1-((1-cyano-1-methylethyl)azo)-formamide, 2-phenylazo-4-methoxy-2,4-dimethylvaleronitrile, dimethyl 2,2'-azobis(2-methylpropionate), 4,4'-azobis(4-cyanovaleric acid) and 2,2'-azobis(2-(hydroxymethyl)propionitrile). If a water-soluble or slightly water-soluble initiator, such as peroxides, hydroperoxides and persulfates, is chosen, it results in polymerization starting in the hydrophilic phase and propagating into the hydrophobic phase. Persulfates, in particular ammonium persulfate, sodium persulfate and potassium persulfate, are soluble in the aqueous phase. Under the action of heat, they decompose and generate anions possessing sulfate radicals, which will contribute to charging the composite nanosphere. Hydrogen peroxide is soluble in the aqueous phase and generates uncharged hydroxyl radicals. The decomposition of hydroperoxides generates a hydroxyl and an oxygen-comprising radical which will be distributed in one of the phases according to the nature of the peroxide used. Thus, cumene peroxide, in the case of the polymerization of styrene, is believed to decompose at the interface between the particles of monomers and the water, the hydroxyl radicals enter the aqueous phase and the nonpolar radicals diffuse toward the particle. The cationic or anionic nature of the particle and of the conjugate resulting from the invention will depend on the cationic or anionic nature of the initiator.

The initiator is introduced into the hydrophilic phase and penetrates into the hydrophobic phase (a) either simultaneously with the introduction of the hydrophobic monomers, (b) or prior to the stage of introduction of the hydrophobic monomers, (c) or subsequent to the stage of introduction of said hydrophobic monomers.

In a preferred embodiment, the polymerization stage (iii) and optionally stage (iv) are carried out by raising the temperature up to approximately 60 to 90° C., in particular to a temperature of 70° C., in the presence of the polymerization initiator, it being understood that the conditions of the polymerization will be determined by a person skilled in the art according to the nature of the initiator selected, or by photochemistry using radiation, for example ultraviolet radiation or a laser beam or other sources of energy.

The organic phase is a phase comprising an aliphatic or cyclic hydrocarbon chosen from compounds comprising from 5 to 12 carbon atoms, their isomers and their mixtures, or a phase comprising all or part of an organic compound which can be polymerized by the radical route. Preferably, the hydrocarbon is chosen from pentane, hexane, heptane, octane, nonane, decane, undecane and dodecane and the organic compound which can be polymerized by the radical route is chosen from water-insoluble vinylaromatic monomers, such as styrene, methylstyrene, ethylstyrene, tert-butylstyrene or vinyltoluene, and the copolymers of these monomers with one another, it being understood that it is within the scope of a person skilled in the art to adjust the polymerization conditions depending on the choice of the hydrocarbon(s) selected and the nature of the initiator chosen. In particular, if the polymerization is carried out by raising the temperature or brings about a rise in temperature, the reaction arrangement should be suitable for volatile solvents, such as pentane.

Preferably, the hydrophilic phase is an aqueous phase, such as water.

In preferred embodiments of the present invention, the functionalization of the particles can be brought to completion by introduction into the phase B and penetration into the phase A of reactive functional groups. The reactive functional groups are introduced, for example, by weakly hydrophilic monomers capable of polymerizing with the hydrophobic monomers of the polymer matrix. In particular, the reactive functional groups are introduced by hydrophilic monomers chosen from acrylic acid, methacrylic acid, ethylenic acid and sulphonic acid monomers, alone or as a mixture, or also as a mixture with hydrophobic monomers; it being understood that it is within the scope of a person skilled in the art to determine the composition of the mixture. The functional groups make possible the subsequent reactions but also introduce the colloidal stabilization necessary for the subsequent applications. The functional groups are introduced into the phase B and penetrate inside the phase A (a) either simultaneously with the penetration of the hydrophobic monomers of stage (ii), (b) or prior to the penetration of the hydrophobic monomers of stage (ii), (c) or subsequent to the penetration of the hydrophobic monomers of stage (ii).

In a specific embodiment, and if desired, stage (iii) is followed by a stage of partial or complete evaporation of the organic phase A with formation of porous composite particles.

The invention thus provides composite particles which are functionalized by the hydrophilic part of the amphiphilic copolymer and which can in addition be functionalized by the presence of reactive functional groups introduced as indicated above during the preparation process. The particles of the invention are preferably functionalized by groups, chosen from carboxyl, amine, thiol, hydroxyl, tosyl or hydrazine groups, which will be able to react with at least one ligand.

The nonporous or porous functionalized composite particles thus formed will be capable of immobilizing a ligand, for example a biological molecule, such as an antibody, an antibody fragment, a protein, a polypeptide, an enzyme, a polynucleotide, a probe, a primer or a nucleic acid fragment; or chemical molecules, such as chemical polymers, medicinal substances, cage molecules, chelating agents, catalysts or biotin; it being understood that, when the composite particles are described as "porous", they have reached a predetermined degree of porosity by complete or partial evaporation of the organic phase.

Consequently, another subject matter of the present invention is conjugates composed of composite particles of the invention, the reactive groups of which have reacted, directly or indirectly, with at least one ligand as defined above, and their uses.

By way of example, said conjugates are used in immunological tests for the detection and/or quantification of proteins, antigens or antibodies in a biological sample or in tests using probe technology for the detection and/or quantification of a nucleic acid fragment in a biological sample. The use of probes for the detection and/or quantification of a nucleic acid in a sample is well known to a person skilled in the art and mention may be made, by way of illustration, of the sandwich hybridization technique. Likewise, the conjugates of the invention can be used as "primer-bearing agents" for a reaction for the amplification of nucleic acids in a sample, for example by PCR (Polymerase Chain Reaction) or any other appropriate amplification technique, thus making possible the detection and/or quantification of nucleic acids in the biological sample.

Another subject matter of the present invention is thus a diagnostic reagent and composition additionally comprising said conjugates and the use of said reagent in a diagnostic test.

The conjugates also find an application in the therapeutic field as vehicle or carrier for a medicinal substance, for a defective gene repair agent, for an agent capable of blocking the expression of a gene, such as an antisense probe, in therapeutics, or for an agent capable of blocking the activity of a protein and, for this reason, they can be used in a therapeutic or prophylactic composition.

Thus, the conjugates of the invention are capable of carrying a medicinal substance in a therapeutic or prophylactic composition which comprises said conjugate in combination with an appropriate and pharmaceutically acceptable adjuvant and/or diluent and/or excipient, said medicinal substance being capable of being released in vivo. The definitions of pharmaceutically acceptable excipients and adjuvants are described, for example, in Remington's Pharmaceutical Sciences, 16th Ed., Mack Publishing Co.

The conjugates of the invention are also capable of carrying a gene of therapeutic interest coding for at least one protein of interest or one fragment of a protein of interest, it being understood that the term "protein" is understood to mean both a protein within the definition thereof most generally used and an antibody. Of course, such a conjugate is incorporated in a therapeutic or prophylactic composition which also comprises the elements necessary for the expression of said gene of therapeutic interest.

The conjugates of the invention can also be used, when incorporated in a therapeutic or prophylactic composition, for the in vivo transfer of antisense probes or oligonucleotides. Antisense sequences are capable of interfering specifically with the synthesis of a target protein of interest by inhibition of the formation and/or functioning of the polysome according to the positioning of the mRNA in the target. Thus, the frequent choice of the sequence surrounding the translation initiation codon as target for inhibition by an antisense oligonucleotide is aimed at preventing the formation of the initiation complex. Other mechanisms in the inhibition by antisense oligonucleotides involve activation of ribonuclease H, which digests antisense oligonucleotide/mRNA hybrids, or interference at splice sites by antisense oligonucleotides, the target of which is an mRNA splice site. Antisense oligonucleotides are also complementary to DNA sequences and can therefore interfere with transcription by the formation of a triple helix, the antisense oligonucleotide pairing via "Hoogsteen" hydrogen bonds in the major groove of the DNA double helix. In this specific case, the term is more accurately "anti-gene oligonucleotides". It is clearly understood that the antisense oligonucleotides can be strictly complementary to the DNA or RNA target to which they have to hybridize but also not strictly complementary, provided that they hybridize to the target. Likewise, they can be antisense oligonucleotides which are unmodified or modified at the internucleotide bonds. All these notions form part of the general knowledge of a person skilled in the art.

The present invention thus relates to a therapeutic composition comprising, inter alia, a conjugate which carries an antisense oligonucleotide as defined above.

Finally, the conjugates are capable of forming complexes of the cage molecule/cryptate or chelating agent/chelated molecule type or of acting as vehicle for catalysts in a chemical application.

The composite particles of the invention are obtained by in situ emulsion polymerization according to the protocol described in the following examples.

EXAMPLE 1

Preparation of a Stable and Isodisperse Emulsion

A stable and isodisperse starting emulsion was prepared in accordance with one or other of the protocols described in this example.

(i) The primary emulsion was prepared using an emulsification process by gradually incorporating, while shearing using a colloid mill (Ika: trade name), the dispersed phase, formed of 45% by weight of iron oxides in octane, in the continuous phase, formed of sodium dodecyl sulfate at a concentration of 50% by weight in water, until fractions comprising 80% by weight of organic ferrofluid are obtained. The mixture thus defined was comminuted in a Couette viscometer of PG398 type at a predetermined shear rate. The primary emulsion thus prepared is a polydisperse emulsion, characterized by a broad distribution in the diameter of the droplets, which is subsequently treated by successive magnetic sortings in order to obtain the starting emulsion which is isodisperse in size.

(ii) The primary emulsion was prepared using an emulsification process by rapidly adding the dispersed phase, formed of octane, of 73% by weight of iron oxides and of a lipophilic surface-active agent of monoglycerol or polyglycerol polyricinoleate type (1 to 10% by weight), to the continuous phase, formed of surfactant of Tergitol NP10 type (31% by weight), using a spatula. The mixture thus defined is subsequently comminuted in a Couette viscometer of PG398 type at a predetermined shear rate. The primary emulsion thus prepared is a relatively isodisperse emulsion, characterized by a low distribution in the diameter of the droplets, which is subsequently treated by successive magnetic sortings in order to obtain the starting emulsion which is isodisperse in size.

EXAMPLE 2

Preparation of Composite Particles with a "Comb" Amphiphilic Copolymer

The emulsion prepared according to the protocol described in example 1(i) (50 ml; Ts=5%), initially stabilized in Triton X405 (2 g/l), is washed three times by magnetic separation with a polymer solution (1.5 g/l; pH 8). At each washing, the clear supernatant is removed and replaced by an equal volume of solution comprising the copolymer. The amphiphilic copolymer is a poly(acrylic acid) modified by hydrophobic linkages (Mw=20000 g/mol). This polymer is composed of 90% of acrylic acid units and of 10% of aryl/polyoxyalkylene methacrylate units (Coatex JS3879B). The copolymer has amphiphilic properties which allow it to be adsorbed at the water/oil interfaces. After having been filtered through a 1 µm Nylon filter, the emulsion is introduced into a 50 ml reactor and degassed under nitrogen for 2 hours with gentle stirring (200 revolutions/min). Styrene (0.3 g), in which 2,2'-azobis(2,4-dimethylvaleronitrile) (4 mg) is dissolved, is then added to the reactor using a syringe. The combined mixture is left stirring (200 revolutions/min) at ambient temperature for one hour. Raising the temperature up to 70° C. brings about decomposition of initiator and initiates the polymerization in the drops of emulsion. The polymerization lasts 15 hours and makes it possible to obtain a stable carboxylic magnetic latex composed of polystyrene particles including iron oxide grains.

EXAMPLE 3

Preparation of Composite Particles with a Diblock Amphiphilic Copolymer

The emulsion prepared according to the protocol described in example 1(i) (50 ml; Ts=5%), initially stabilized in Triton X405 (2 g/l), is washed three times by magnetic separation with the preceding copolymer solution (0.8 g/l, pH 8). This copolymer was obtained according to a controlled radical polymerization process. It has a mass of approximately 20000 g/mol. The polystyrene block represents approximately 10% of the mass of the polymer. At each washing, the clear supernatant is removed and replaced by an equal volume of solution comprising the copolymer. After having been filtered through a 1 µm Nylon filter, the emulsion is introduced into a 50 ml reactor and degassed under nitrogen for 2 hours with gentle stirring (200 revolutions/min). Styrene (0.3 g) and 2,2'-azobis(2,4-dimethylvaleronitrile) (6 mg) are then added to the reactor using a syringe. The combined mixture is left stirring (200 revolutions/min) at ambient temperature for one hour. Raising the temperature up to 70° C. brings about decomposition of the initiator and initiates the polymerization in the drops of emulsion. The polymerization lasts 15 hours and makes it possible to obtain a stable carboxylic magnetic latex composed of polystyrene particles including iron oxide grains.

EXAMPLE 4

Preparation of Composite Particles with a Diblock Amphiphilic Copolymer

The emulsion prepared according to the protocol described in example 1(i) (50 ml; Ts=5%), initially stabilized in Triton X405 (2 g/l), is washed twice by magnetic separation with the preceding copolymer solution (0.4 g/l; pH 8). The poly(acrylic acid) block was obtained by controlled radical polymerization. The polymer has a mass of 18600 g/mol and the polyethylene block represents approximately 2% of this mass. At each washing, the clear supernatant is removed and replaced by an equal volume of solution comprising the copolymer. After having been filtered through a 1 µm Nylon filter, the emulsion is introduced into a 50 ml reactor and degassed under nitrogen for 2 hours with gentle stirring (200 revolutions/min). Styrene (0.3 g) and 2,2'-azobis(2,4-dimethylvaleronitrile) (6 mg) are then added to the reactor using a syringe. The combined mixture is left stirring (200 revolutions/min) at ambient temperature for one hour. Raising the temperature up to 70° C. brings about decomposition of the initiator and initiates the polymerization in the drops of emulsion. The polymerization lasts 14 hours and makes it possible to obtain a stable carboxylic magnetic latex composed of polystyrene particles including iron oxide grains.

EXAMPLE 5

Preparation of Composite Particles with a "Comb" Amphiphilic Copolymer, the Hydrophobic Part of Which is Immobilized at the Surface of the Polymer Matrix (i) Production of the Latex 20 ml of the stable and isodisperse starting emulsion prepared according to the protocol of example 1(i) and composed of two immiscible phases: the phase A, composed of droplets with a diameter of 180 nm plus or minus 5 nm comprising iron oxide nanoparticles with a diameter of 10 nm in octane and a mixture of surfactants (sodium dodecyl sulfate (SDS) and oleic acid), dispersed in the aqueous phase B (1% concentration, at 0.8 times the critical micelle concentration (CMC) of SDS), are placed in a polymerization reactor. The emulsion is degassed for 7 hours under nitrogen. 2,2'-azobis(2,4-dimethylvaleronitrile), as initiator of the polymerization, dissolved in hexane (215 µl at 20 g/l), is introduced into the emulsion. The mixture is subjected to homogenization for one hour and 80 mg of styrene monomers are subsequently introduced. The styrene monomers diffuse inside the phase A for two hours. The polymerization is initiated by heating the solution to a temperature of 70° C. and is continued for 12 hours 30 minutes with slow stirring. After completion of the polymerization, the composite particles obtained exhibit a diameter of 188 nm and a polydispersity index of the order of 1.1.

(ii) Immobilization of the Amphiphilic Copolymer

Polystyrene magnetic latex particles obtained in (i) (45 ml) are washed twice with a solution of Coatex polymer (MW=20000 g/mol; 0.8 g/l; pH 3.4) by successive magnetic separations. The latex thus washed is introduced (44 ml; Ts=3.8%) into the polymerization reactor. The reaction medium is degassed with nitrogen for two hours with stirring (200 revolutions/min). Styrene (0.3 g) is introduced and swelling is allowed to take place for one hour with stirring at 200 revolutions/min. The temperature is raised to 70° C. and then potassium persulfate (KPS) (6 mg in 1 ml of MilliQ water) is introduced. The polymerization is then carried out at 70° C. for 7 hours with stirring at 200 revolutions/min.

EXAMPLE 6

Preparation of Composite Particles with a Diblock Amphiphilic Copolymer, the Hydrophobic Part of Which is Immobilized at the Surface of the Polymer Matrix Polystyrene magnetic latex particles (45 ml, obtained by in situ polymerization of an emulsion with a conventional styrene/water-insoluble initiator mixture in accordance with example 5(i)) are washed twice with a solution of diblock polymer (MW=10000 g/mol; 0.8 g/l; pH=3.4) by successive magnetic separations. The latex thus washed is introduced (40 ml; Ts=3.4%) into the polymerization reactor. The reaction medium is degassed with nitrogen for 2 hours with stirring (200 revolutions/min). Styrene (0.3 g) is introduced and swelling is allowed to take place for one hour with stirring at 200 revolutions/min. The temperature is raised to 70° C. and then potassium persulfate (KPS) (4 mg in 0.2 ml of MilliQ water) is introduced. The polymerization is then carried out at 70° C. for 16 hours with stirring at 200 revolutions/min.

EXAMPLE 7

Preparation of Composite Particles with a "Comb" Amphiphilic Copolymer

The magnetic emulsion prepared as indicated in example 1(i) (diameter 220 nm and concentration 4% mass/volume) is stabilized with a comb amphiphilic copolymer, poly (acrylic acid) modified by hydrophobic linkages (MW=50000 g/mol) composed of 80% of acrylic acid units and 20% of aryl/polyoxyalkylene methacrylate units (Coatex M883), at a concentration of 0.05% and is placed in a polymerization reactor. Six mg of AIBN (2,2'-azobisisobutyronitrile), 360 mg of styrene and 240 mg of divinylbenzene are added and incubated for 1 hour at 20° C. The polymerization is brought about by raising the temperature to 70° C. for 13 hours. The final magnetic latex has a size of the order of 240 nm.

EXAMPLE 8

Preparation of Composite Particles

The magnetic emulsion as prepared in example 1(i) is stabilized in 0.2% Triton X-405 and is then washed three times with a solution of the polymer as described in example 7 (Coatex M883; MW=50000 g/mol) at a concentration of 0.05%.

EXAMPLE 9

Grafting of Streptavidin

100 μl of phosphate buffer (10 mM, pH 6.8) were added to 0.5 mg of the particles as obtained in the preceding examples 7 and 8. The particles were stirred and then magnetized. The particles were taken up in 50 μl of phosphate buffer. 15 μl of streptavidin (5 mg/ml) were mixed with 50 μl of water-soluble carbodiimide (1 mg/ml) in an Eppendorf tube. Stirring was carried out at 300 revolutions/min for 2 minutes and then the particles were added to the tube. Incubation was carried out at 40° C. and 1000 revolutions/min for 30 minutes and then 100 μl of blocking buffer (PBS+Triton X-405+ethanolamine) were added. The mixture was incubated at 40° C. and 1000 revolutions/min for 30 minutes. The particles were then magnetized and were then taken up in 100 μl of storage buffer (PBS+Triton X-405). Two fresh washing operations were carried out with this storage buffer. During a final washing operation, the particles were taken up in 50 μl of storage buffer.

EXAMPLE 10

Grafting a Biotinylated Oligonucleotide to the Particle-Streptavidin Conjugate

The particles (0.25 mg) of the conjugates as obtained in the preceding example 9 were magnetized and were taken up in 50 μl of TE NaCl buffer (Tris 10 mM, EDTA 1 mM, NaCl 1M, Triton X-405 0.05%, salmon DNA). $2.2 \times 10^{13}$ copies of biotinylated oligonucleotide (ODN) were added. Incubation was carried out at 37° C. and 1000 revolutions/min for 30 minutes. The particles were magnetized and were taken up in 50 μl of TE NaCl buffer.

EXAMPLE 11

Hybridization and Demonstration of the Coupling

100 μl of TE NaCl buffer were added to 40 μg of the conjugates as obtained in the preceding example 10. $18 \times 10^{10}$ copies of target oligonucleotide and $18 \times 10^{10}$ copies of detection oligonucleotide labeled with horseradish peroxidase were added. Incubation was carried out at 37° C. and 1000 revolutions/min for 30 minutes. Washing was carried out three times in the TE NaCl buffer. 100 μl of o-phenylenediamine (OPD) (dilution of 5 mg of OPD in 2.5 ml of Coloreia diluent) were added. Incubation was carried out for 3 minutes. 100 μl of 1N $H_2SO_4$ were added and then the particles were magnetized. 100 μl of supernatant were withdrawn and its intensity at 492 nm was analyzed. The negative control is composed of target-free conjugates. The results are shown in the following table:

| | Negative control | Test 1 | Test 2 |
|---|---|---|---|
| Conjugates of example 8 | 0.266 | 0.848 | 0.871 |
| Conjugates of example 9 | 0.242 | 0.822 | 0.824 |

What is claimed is:

1. A composite particle comprising a core made of a hydrophobic polymer and inorganic nanoparticles, said hydrophobic polymer constituting a polymer matrix within which the inorganic nanoparticles are stabilized and distributed homogeneously, said particle being characterized in that it is at least partially surrounded by an amphiphilic copolymer comprising a hydrophobic part and a hydrophilic part, the hydrophobic part of which is at least partially immobilized on or in said polymer matrix.

2. The particle as claimed in claim 1, characterized in that it is completely surrounded by an amphiphilic copolymer.

3. The particle as claimed in claim 1, characterized in that all of the hydrophobic part of the amphiphilic copolymer is immobilized on or in the polymer matrix.

4. The particle as claimed in claim 1, characterized in that the hydrophobic part of the amphiphilic copolymer is selected from the group consisting of: polystyrenes, polyalkyls and fatty acid chains.

5. The particle as claimed in claim 1, characterized in that the hydrophilic part of the amphiphilic copolymer is selected from the group consisting of: poly(acrylic acid)s, polysulfates, polyamines, polyamides and polysaccharides.

6. The particle as claimed in claim 1, characterized in that the amphiphilic copolymer is selected from the group consisting of: block polymers, sequential polymers, branched polymers and comb polymers.

7. The particle as claimed in claim 6, characterized in that it exhibits reactive functional groups at its surface capable of reacting with at least one ligand.

8. A conjugate, characterized in that it is composed of the composite particle as defined in claim 7, the functional groups of which have interacted, directly or indirectly, with at least one ligand selected from the group consisting of: antibodies, antibody fragments, proteins, polypeptides, enzymes, polynucleotides, nucleic acid fragments and biotin.

9. A reagent comprising at least one conjugate as defined in claim 8.

10. A conjugate, characterized in that it is composed of the composite particle as defined in claim 7, the functional groups of which have interacted, directly or indirectly, with at least one ligand selected from the group consisting of: cage molecules, chelating agents and catalysts.

11. A conjugate, characterized in that it is composed of the composite particle as defined in claim 7, the functional groups of which have interacted, directly or indirectly, with at least one ligand selected from the group consisting of: medicinal substances, antisense probes, gene repair agents, agents for blocking a protein activity and agents for inhibiting a protein activity.

12. A therapeutic composition comprising the conjugate as defined in claim 11.

13. The particle as claimed in claim 7, characterized in that the reactive functional groups are selected from the group consisting of: carboxyl groups, amine groups, thiol groups, aldehyde groups, hydroxyl groups, tosyl groups and hydrazine groups.

14. The particle as claimed in claim 1, characterized in that the nanoparticles are composed of inorganic materials selected from the group consisting of: iron, titanium, cobalt, zinc, copper, manganese, chromium and nickel metal oxides; magnetizable metal oxides; magnetite; hematite; ferrites; and alloys of cobalt and alloys of nickel.

15. The particle as claimed in claim 14, characterized in that the inorganic materials are magnetizable metal oxides selected from the group consisting of: iron oxide, magnetite and hematite.

16. The particle as claimed in claim 14, characterized in that the inorganic materials represent from 5 to 95% by mass, with respect to the total mass of said particle.

17. The particle as claimed in claim 16, characterized in that the inorganic materials represent from 25 to 85% by mass, with respect to the total mass of said particle.

18. The particle as claimed in claim 1, characterized in that the inorganic nanoparticles are stabilized by stabilizing agents selected from the group consisting of: ionic groups, polymer chains, surface-active agents, functional surface-active agents and mixtures of surface-active agents.

19. The particle as claimed in claim 18, characterized in that the surface-active agents are selected from the group consisting of: sodium dodecyl sulfate and mixtures of sodium dodecyl sulfate and oleic acid.

20. The particle as claimed in claim 1, characterized in that the polymer matrix is a matrix of hydrophobic vinylaromatic polymer types selected from the group consisting of: homopolymers of water-insoluble vinylaromatic monomers, copolymers of water-insoluble vinylaromatic monomers with one another, copolymers of water-insoluble vinylaromatic monomers with one another and with other water-insoluble polymerizable monomers and copolymers of water-insoluble vinylaromatic monomers with other water-insoluble polymerizable monomers.

21. The particle as claimed in claim 20, characterized in that the polymer is a crosslinked polymer.

22. The particle as claimed in claim 20, characterized in that the water-insoluble vinylaromatic monomers are selected from the group consisting of: styrene, methylstyrene, ethylstyrene, tert-butylstyrene and vinyltoluene.

23. The particle as claimed in claim 20, characterized in that the other water-insoluble polymerizable monomers are selected from the group consisting of: alkyl acrylates and methacrylates, wherein the alkyl group comprises from 3 to 10 carbon atoms; alkyl esters of ethylenic acids, wherein the ethylenic acid possesses 4 or 5 carbon atoms and the alkyl group possesses 1 to 8 carbon atoms; methacrylic acids; styrene derivatives; and diene compounds.

24. The particle as claimed in claim 1, characterized in that it additionally comprises a radioactive tracer.

25. The particle as claimed in claim 1, characterized in that it exhibits a diameter of the order of approximately 50 to 1000 nm.

26. The particle as claimed in claim 25, characterized in that it exhibits a diameter of the order of approximately 100 to 250 nm.

27. A process for the preparation of the composite particle as claimed in claim 1 for which the hydrophobic part of the amphiphilic copolymer is at least partially immobilized in the polymer matrix, characterized in that
(i) a stable and isodisperse starting emulsion composed of two immiscible phases, a hydrophobic phase A composed of droplets comprising inorganic nanoparticles dispersed in an organic phase comprising a surface-active agent and a hydrophilic phase B in which phase A is dispersed, is present;
(ii) hydrophobic monomers and at least one initiator are introduced into phase B; and
(iii) said hydrophobic monomers are polymerized inside phase A,
said process being characterized in that, before stage (iii), at least one amphiphilic copolymer is additionally introduced into the-phase B.

28. The process as claimed in claim 27, characterized in that the amphiphilic copolymer is introduced before or after stage (ii).

29. The process as claimed in claim 27, characterized in that the amphiphilic copolymer is selected from the group consisting of: block polymers, sequential polymers, branched polymers and comb polymers.

30. The process as claimed in claim 27, characterized in that the hydrophobic monomers are selected from the group consisting of: vinylaromatic monomers, mixtures of vinylaromatic monomers and mixtures of vinylaromatic monomers with other water-insoluble polymerizable monomers.

31. The process as claimed in claim 30, characterized in that a hydrophobic crosslinking agent is added to the monomer or to the mixture of monomers.

32. The process as claimed in claim 30, characterized in that the vinylaromatic monomers are selected from the group consisting of: styrene, methylstyrene, ethylstyrene, tert-butylstyrene and vinyltoluene.

33. The process as claimed in claim 30, characterized in that the other water-insoluble polymerizable monomers are selected from the group consisting of: alkyl acrylates, alkyl methacrylates, alkyl esters of ethylenic acids, methacrylic acids, styrene derivatives, ethylenic acids and diene compounds.

34. The process as claimed in claim 27, characterized in that the initiator is selected from the group consisting of: organosoluble initiators, initiators that are weakly soluble in the hydrophilic phase and initiators that are soluble in the hydrophilic phase.

35. The process as claimed in claim 34, characterized in that the organosoluble initiator is an azobis type initiator selected from the group consisting: 2,2'-azobis(2,4-dimethylvaleronitrile), 2,2'-azobis(4-methoxy-2,4-dimethylvaleronitrile), 2,2'-azobis(2-cyclopropylpropionitrile), 2,2'-azobis(2-methylpropionitrile), 2,2'-azobis(2-methylbutyronitrile), 1,1'-azobis(cyclohexane-1-carbonitrile), 1-((1-cyano-1-methylethyl)azo) formamide, 2-phenylazo-4-methoxy-2,4-dimethylvaleronitrile, dimethyl 2,2'-azobis(2-methylpropionate), 4,4'-azobis(4-cyanovaleric acid) and 2,2'-azobis(2-(hydroxymethyl)propionitrile).

36. The process as claimed in claim 34, characterized in that the initiator is a weakly soluble or soluble in the hydrophilic phase radical initiator selected from the group consisting of: peroxides, hydroperoxides and persulfates.

37. The process as claimed in claim 27, characterized in that the initiator is introduced into the hydrophilic phase either simultaneously with the introduction of the hydrophobic monomers or before or after the introduction of said monomers.

38. The process as claimed in claim 27, characterized in that the polymerization (iii) is carried out by photochemistry.

39. The process as claimed in claim 27, characterized in that the organic phase of phase A comprises an aliphatic or cyclic hydrocarbon selected from the group consisting of: compounds comprising from 5 to 12 carbon atoms, isomers of compounds comprising from 5 to 12 carbon atoms and mixtures of compounds comprising from 5 to 12 carbon atoms, or the organic phase of phase A comprises all or part of an organic compound that can be polymerized by the radical route selected from the group consisting of: water-insoluble vinylaromatic monomers and copolymers of water-insoluble vinylaromatic monomers with one another.

40. The process as claimed in claim 39, characterized in that the hydrocarbon is selected from the group consisting of: pentane, hexane, heptane, octane, nonane, decane, undecane and dodecane, and the organic compound that can be polymerized by the radical route is selected from the group consisting of: styrene, methylstyrene, ethylstyrene, tert-butylstyrene, vinyltoluene, and copolymers of these monomers with one another.

41. The process as claimed in claim 39, characterized in that the water-insoluble vinylaromatic monomers are selected from the group consisting of: styrene, methylstyrene, ethylstyrene, tert-butylstyrene and vinyltoluene.

42. The process as claimed in claim 27, characterized in that phase B is an aqueous phase.

43. The process as claimed in claim 27, characterized in that it additionally comprises a stage of functionalization of the composite particle by penetration into phase A of reactive functional groups introduced by weakly hydrophilic monomers capable of polymerizing with the hydrophobic monomers.

44. The process as claimed in claim 43, characterized in that the reactive functional groups are acid groups introduced by weakly hydrophilic monomers selected from the group consisting of: acrylic acid, methacrylic acid, ethylenic acid and sulphonic acid monomers, or by polymerizable monomers selected from the group consisting of: water-insoluble vinylaromatic monomers, copolymers of vinylaromatic monomers with one another and copolymers of vinylaromatic monomers with other hydrophobic monomers.

45. The process as claimed in claim 44, characterized in that the water-insoluble vinylaromatic monomers are selected from the group consisting of: styrene, methylstyrene, ethylstyrene, tert-butylstyrene and vinyltoluene.

46. The process as claimed in claim 43, characterized in that weakly hydrophilic monomers are introduced into the phase A either simultaneously with the introduction of the hydrophobic monomers or before or after the introduction of said monomers.

47. The process as claimed in claim 27, characterized in that it additionally comprises, after the polymerization stage (iii), a stage of complete or partial evaporation of phase A.

48. A process for the preparation of the composite particle as claimed in claim 1 and for which the hydrophobic part of the amphiphilic copolymer is at least partially immobilized on the polymer matrix, characterized in that
   (i) a stable and isodisperse starting emulsion composed of two immiscible phases, a hydrophobic phase A composed of droplets comprising inorganic nanoparticles dispersed in an organic phase comprising a surface-active agent and a hydrophilic phase B in which phase A is dispersed, is present;
   (ii) hydrophobic monomers and at least one initiator are introduced into phase B; and
   (iii) a fraction of said hydrophobic monomers is polymerized inside phase A,
   said process being characterized in that, before stage (iii) or after stage (iii), at least one amphiphilic copolymer is additionally introduced into phase B and then, according to a stage (iv), the remaining fraction of the hydrophobic monomers is polymerized at the surface of the polymer matrix.

49. The process as claimed in claim 48, characterized in that, when the amphiphilic copolymer is introduced before stage (iii), it is introduced before or after stage (ii).

50. The process as claimed in claim 48, characterized in that the polymerization (iii) and/or (iv) is carried out by heating to a temperature of approximately 60 to 90° C.

* * * * *